(12) United States Patent
Kim et al.

(10) Patent No.: US 8,058,451 B2
(45) Date of Patent: *Nov. 15, 2011

(54) HYDROXYCUCURBITURIL DERIVATIVES, THEIR PREPARATION METHODS AND USES

(75) Inventors: Ki-Moon Kim, Pohang-shi (KR); Sang-Yong Jon, Pohang-shi (KR); Narayanan Selvapalam, Pohang-shi (KR); Dong-Hyun Oh, Pohang-shi (KR)

(73) Assignee: Postech Foundation, Pohang-shi, Kyungsangbuk-do (KR)

( * ) Notice: Subject to any disclaimer, the term of this patent is extended or adjusted under 35 U.S.C. 154(b) by 324 days.

This patent is subject to a terminal disclaimer.

(21) Appl. No.: 12/138,883

(22) Filed: Jun. 13, 2008

(65) Prior Publication Data

US 2008/0260676 A1    Oct. 23, 2008

Related U.S. Application Data

(62) Division of application No. 10/497,464, filed as application No. PCT/KR02/02213 on Nov. 26, 2002, now Pat. No. 7,388,099.

(30) Foreign Application Priority Data

Jan. 3, 2002    (KR) ..................... 2002-318
Nov. 6, 2002   (KR) ................. 2002-68362

(51) Int. Cl.
    *C07D 403/02*    (2006.01)
(52) U.S. Cl. ................................... 548/305.4
(58) Field of Classification Search ............ 548/305.4
    See application file for complete search history.

(56) References Cited

U.S. PATENT DOCUMENTS 7,388,099 B2 *   6/2008   Kim et al. ............... 548/305.4

FOREIGN PATENT DOCUMENTS

| AU | 23299 A | 6/1999 |
| DE | 4001139 A | 10/1990 |
| DE | 19603377 A | 8/1997 |
| JP | 2001-122877 | * 5/2001 |
| JP | 2001-122877 A | 5/2001 |
| WO | 00/68232 A1 | 11/2000 |

OTHER PUBLICATIONS

Anthony et al., Angew. Chem. Int. Ed. Engl., 31. No. 11, pp. 1475-1477, 1992.
Kim et al., J. Am. Chem. Soc., vol. 122, No. 3, pp. 540-541, 2000.
Day. A. et al., "Controlling Factors in the Synthesis of Cucurbituril and Its Homologues," J. Org. Chem., vol. 66, No. 24, pp. 8094-8100 (2001).
Kellersberger, K., et al., "Encapsulation of N2, O2, Methanol, or Acetonitrile by Decamethylcucurbit[5]uril(NH4+) 2 Complexes in the Gas Phase: Influence of the Guest on 'Lid' Tightness," J. Am. Chem. Soc., vol. 123, No. 45, pp. 11316-11317 (2001).
Oh, K., et al., "Structural Stabilities and Self-Assembly of Cucurbit[n]uril (n=4-7) and Decamethylcucurbit[n]uril (n=4-6): A Theoretical Study,"J. Phys. Chem. B, vol. 105, No. 40, pp. 9726-9731 (2001).
Witt, D. et al., "Diastereoselective Formation of Methylene-Bridged Glycoluril Dimers," Organic Letters, vol. 2, No. 6, pp. 755-758 (2000).

* cited by examiner

*Primary Examiner* — Paul V. Ward
(74) *Attorney, Agent, or Firm* — Rothwell, Figg, Ernst & Manbeck

(57) ABSTRACT

Provided are hydroxycucurbituril derivatives, their preparation methods and uses. The hydroxycucurbituril derivative is easy to further functionalize with enhanced solubility in common solvents, thereby providing wider applications.

13 Claims, 1 Drawing Sheet

HYDROXYCUCURBITURIL DERIVATIVES, THEIR PREPARATION METHODS AND USES

CROSS REFERENCE TO RELATED APPLICATIONS

The present application is a divisional of U.S. patent application Ser. No. 10/497,464, filed on Jun. 2, 2004, which is a 35 U.S.C. §371 National Phase Entry Application from PCT/KR02/02213, filed Nov. 26, 2002, and designating the U.S., and claims priority under 35 U.S.C. §119 based on Korean Patent Application No. 2002-318 filed Jan. 3, 2002 and Korean Application No. 2002-68362 filed Nov. 6, 2002, which are incorporated herein in their entireties.

BACKGROUND OF THE INVENTION

1. Field of the Invention

The present invention relates to hydroxycucurbituril derivatives, their preparation methods and uses, and more particularly, hydroxycucurbituril derivatives which can easily introduce substituents according to uses, their preparation methods and uses.

2. Description of the Related Art

Cucurbituril was first reported by R. Behrend, E. Meyer and F. Rusche in 1905. According to their report (Liebigs Ann. Chem. 1905, 339, 1.), the condensation of glycoluril and excess formaldehyde in the presence of hydrochloric acid (HCl) produces an amorphous solid. Dissolution of the solid in hot concentrated sulfuric acid, dilution of the solution with water followed by slow cooling of the solution to room temperature produces a crystalline material. They wrongly characterized this substance as $C_{10}H_{11}N_7O_4 \cdot 2H_2O$ without discovery of its structure.

In 1981, this substance was rediscovered by Mock and coworkers. They correctly characterized it as a hexameric macrocyclic compound with composition of $C_{36}H_{36}N_{24}O_{12}$, which was also confirmed by X-ray crystal structure determination (J. Am. Chem. Soc., 1981, 103, 7367). They named it cucurbituril which we from now on refer to as cucurbit[6]uril. Since then an improved preparation procedure for cucurbit[6]uril has been disclosed (DE 196 03 377 A1).

In 2000, Kim and coworkers synthesized novel cucurbit[6]uril homologues thereof, cucurbit[n]uril (n=5, 7, 8) and isolated the same, which were confirmed by X-ray crystal structure determination (J. Am. Chem. Soc., 2000, 122, 540).

WO 00/68232 discloses cucurbit[n]uril having the formula:

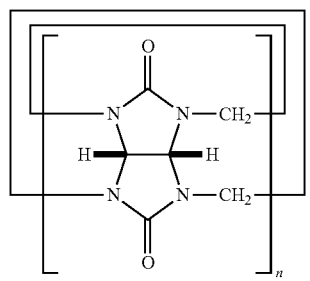

wherein n is an integer between 4 and 20.

The cucurbituril derivatives are compounds of substitutent-free glycoluril monomers.

A cucurbituril derivative synthesized from glycoluril having a substituent introduced thereto has been reported (Angew. Chem. Int. Ed. Engl. 1992, 31, 1475). According to this report, decamethylcucurbit[5]uril was synthesized using five dimethanodimethylglycoluril units forming a cyclic structure by the condensation of dimethylglycoluril and formaldehyde.

However, in the cucurbiturils and their derivatives proposed up to now, it is not easy to introduce functional groups thereto by substitution, and thus their applications are limited. Also, in order to produce substituted cucurbituril derivatives, different glycoluril monomers must be synthesized and subjected to cyclization, making their synthetic methods complex.

SUMMARY OF THE INVENTION

To solve the above problems, an objective of the present invention is to provide hydroxycucurbituril derivatives, which can easily introduce suitable substitutents according to uses.

It is another objective of the present invention to provide preparation methods of the hydroxycucurbituril derivatives.

It is still another objective of the present invention to provide uses of the hydroxycucurbituril derivatives.

In an embodiment, the present invention provides hydroxycucurbituril derivatives represented by the formula 1:

[Formula 1]

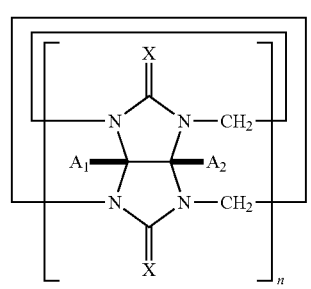

wherein at least one among $nA_1$ and $nA_2$ is selected from the group consisting of hydroxy, substituted or unsubstituted C1-C30 alkyloxy, substituted or unsubstituted C1-C30 alkenyloxy, substituted or unsubstituted C1-C30 alkynyloxy, substituted or unsubstituted C2-C30 carbonylalkyloxy, substituted or unsubstituted C1-C30 thioalkyloxy, substituted or unsubstituted C1-C30 alkylthioloxy, substituted or unsubstituted C1-C30 hydroxyalkyloxy, C1-C30 hydroxyalkyloxy, substituted or unsubstituted C1-C30 alkylsilyloxy, substituted or unsubstituted C1-C30 aminoalkyloxy, substituted or unsubstituted C1-C30 aminoalkylthiolalkyloxy, substituted or unsubstituted C5-C30 cycloalkyloxy, substituted or unsubstituted C2-C30 heterocycloalkyloxy, substituted or unsubstituted C6-C30 aryloxy, substituted or unsubstituted C6-C20 arylalkyloxy, substituted or unsubstituted C4-C30 heteroaryloxy, substituted or unsubstituted C4-C30 heteroarylalkyloxy; substituted or unsubstituted C1-C30 alkylthio, substituted or unsubstituted C1-C30 alkenylthio, substituted or unsubstituted C1-C30 alkynylthio, substituted or unsubstituted C2-C30 carbonylalkylthio, substituted or unsubstituted C1-C30 thioalkylthio, substituted or unsubstituted C1-C30 hydroxyalkylthio, substituted or unsubstituted C1-C30 alkylsilylthio, substituted or unsubstituted C1-C30 aminoalkylthio, substituted or unsubstituted C1-C30 aminoalkylthiolalkylthio, substituted or unsubstituted C5-C30 cycloalkylthio, substituted or unsubstituted C2-C30 heterocycloalkylthio, substituted or unsubstituted C6-C30 arylthio, substituted or unsubstituted C6-C20 arylalkylthio, substituted or unsubstituted C4-C30 heteroarylthio, substituted or unsubstituted C4-C30 heteroarylalkylthio; substituted or unsubstituted C1-C30 alkylamine, substituted or unsubstituted C1-C30 alkenylamine, substituted or unsubstituted C1-C30 alkynylamine, substituted or unsubstituted C2-C30 carbonylalkylamine, substituted or unsubstituted C1-C30 thioalkylamine, substituted or unsubstituted C1-C30 hydroxyalkylamine, substituted or unsubstituted C1-C30 alkylsilylamine, substituted or unsubstituted C1-C30 aminoalkylamine, substituted or unsubstituted C1-C30 aminoalkylthiolalkylamine, substituted or unsubstituted C5-C30 cycloalkylamine, substituted or unsubstituted C2-C30 heterocycloalkylamine, substituted or unsubstituted C6-C30 arylamine, substituted or unsubstituted C6-C20 arylalkylamine, substituted or unsubstituted C4-C30 heteroarylamine, and substituted or unsubstituted C4-C30 heteroarylalkylamine, $A_1$ and $A_2$ are both hydrogen (H), X is O, S or NH, and n is an integer between 4 and 20.

In another aspect, the invention provides methods of preparing hydroxycucurbituril derivatives represented by the formula 1; the methods include alkylation or carboxylation of hydroxycucurbituril represented by the formula 5:

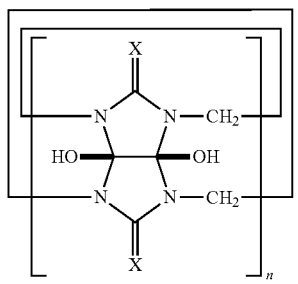

[Formula 5]

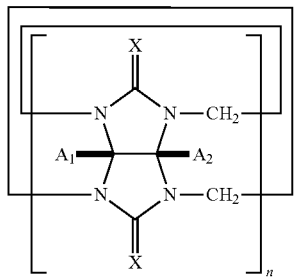

[Formula 1]

wherein $A_1$ is $OR_1$, $A_2$ is $OR_2$, X is O, S or NH, $R_1$ and $R_2$ are independently selected from the group consisting of H, substituted or unsubstituted C1-C30 alkyl, substituted or unsubstituted C1-C30 alkenyl, substituted or unsubstituted C1-C30 alkynyl, substituted or unsubstituted C2-C30 carbonylalkyl substituted or unsubstituted C1-C30 thioalkyl, substituted or unsubstituted, C1-C30 alkylthiol, substituted or unsubstituted C1-C30 alkoxy, substituted or unsubstituted C1-C30 hydroxyalkyl, substituted or unsubstituted C1-C30 alkylsilyl, substituted or unsubstituted C1-C30 aminoalkyl, substituted or unsubstituted C1-C30 aminoalkylthioalkyl, substituted or unsubstituted C5-C30 cycloalkyl, substituted or unsubstituted C2-C30 heterocycloalkyl, substituted or unsubstituted C6-C30 aryl, substituted or unsubstituted C6-C20 arylalkyl, substituted or unsubstituted C4-C30 heteroaryl and substituted or unsubstituted C4-C20 heteroarylakyl, and n is an integer between 4 and 20.

Alternatively, the present invention is achieved by methods of preparing hydroxycucurbituril derivatives represented by the formula 1; the methods include the reaction of hydroxycucurbituril represented by the formula 5 with thiol:

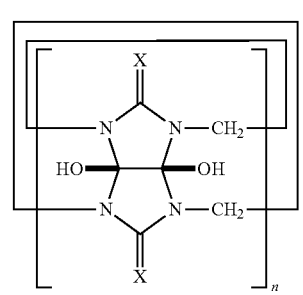

[Formula 5]

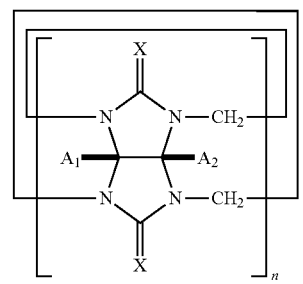

[Formula 1]

wherein $A_1$ is $SR_1$, $A_2$ is $SR_2$, X is O, S or NH, $R_1$ and $R_2$ are independently selected from the group consisting of H, substituted or unsubstituted C1-C30 alkyl, substituted or unsubstituted C1-C30 alkenyl, substituted or unsubstituted C1-C30 alkynyl, substituted or unsubstituted C2-C30 carbonylalkyl, substituted or unsubstituted C1-C30 thioalkyl, substituted or unsubstituted C1-C30 alkylthiol, substituted or unsubstituted C1-C30 alkoxy, substituted or unsubstituted C1-C30 hydroxyalkyl, substituted or unsubstituted C1-C30 alkylsilyl, substituted or unsubstituted C1-C30 aminoalkyl, substituted or unsubstituted C1-C30 aminoalkylthioalkyl, substituted or unsubstituted C5-C30 cycloalkyl, substituted or unsubstituted C2-C30 heterocycloalkyl, substituted or unsubstituted C6-C30 aryl, substituted or unsubstituted C6-C20 arylalkyl, substituted or unsubstituted C4-C30 heteroaryl and substituted or unsubstituted C4-C20 heteroarylakyl, and n is an integer between 4 and 20.

Also, the present invention is achieved by methods of preparing hydroxycucurbituril derivatives represented by the formula 1; the methods include the reaction of hydroxycucurbituril represented by the formula 5 with amine:

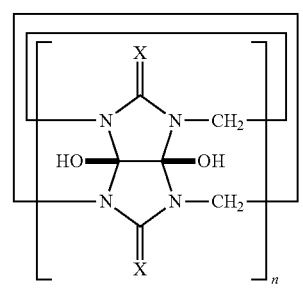

[Formula 5]

-continued

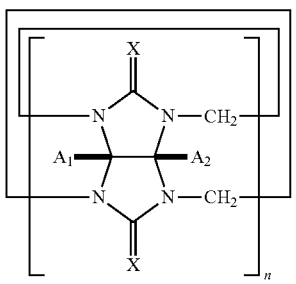
[Formula 1]

wherein $A_1$ is $NHR_1$, $A_2$ is $NHR_2$, X is O, S or NH, $R_1$ and $R_2$ are independently selected from the group consisting of H, substituted or unsubstituted C1-C30 alkyl, substituted or unsubstituted C1-C30 alkenyl, substituted or unsubstituted C1-C30 alkynyl, substituted or unsubstituted C2-C30 carbonylalkyl, substituted or unsubstituted C1-C30 thioalkyl, substituted or unsubstituted C1-C30 alkylthiol, substituted or unsubstituted C1-C30 alkoxy, substituted or unsubstituted C1-C30 hydroxyalkyl, substituted or unsubstituted C1-C30 alkylsilyl, substituted or unsubstituted C1-C30 aminoalkyl, substituted or unsubstituted C1-C30 aminoalkylthioalkyl, substituted or unsubstituted C5-C30 cycloalkyl, substituted or unsubstituted C2-C30 heterocycloalkyl, substituted or unsubstituted C6-C30 aryl, substituted or unsubstituted C6-C20 arylalkyl, substituted or unsubstituted C4-C30 heteroalkyl and substituted or unsubstituted C4-C20 heteroarylakyl, and n is an integer between 4 and 20.

In still another aspect, the present invention also demonstrates an ion sensor employing the hydroxycucurbituril derivatives as ion selective materials.

BRIEF DESCRIPTION OF THE DRAWING

The above and other features and advantages of the present invention will become more apparent by describing in detail exemplary embodiments thereof with reference to the attached drawing in which.

DETAILED DESCRIPTION OF THE INVENTION

Figure 1:
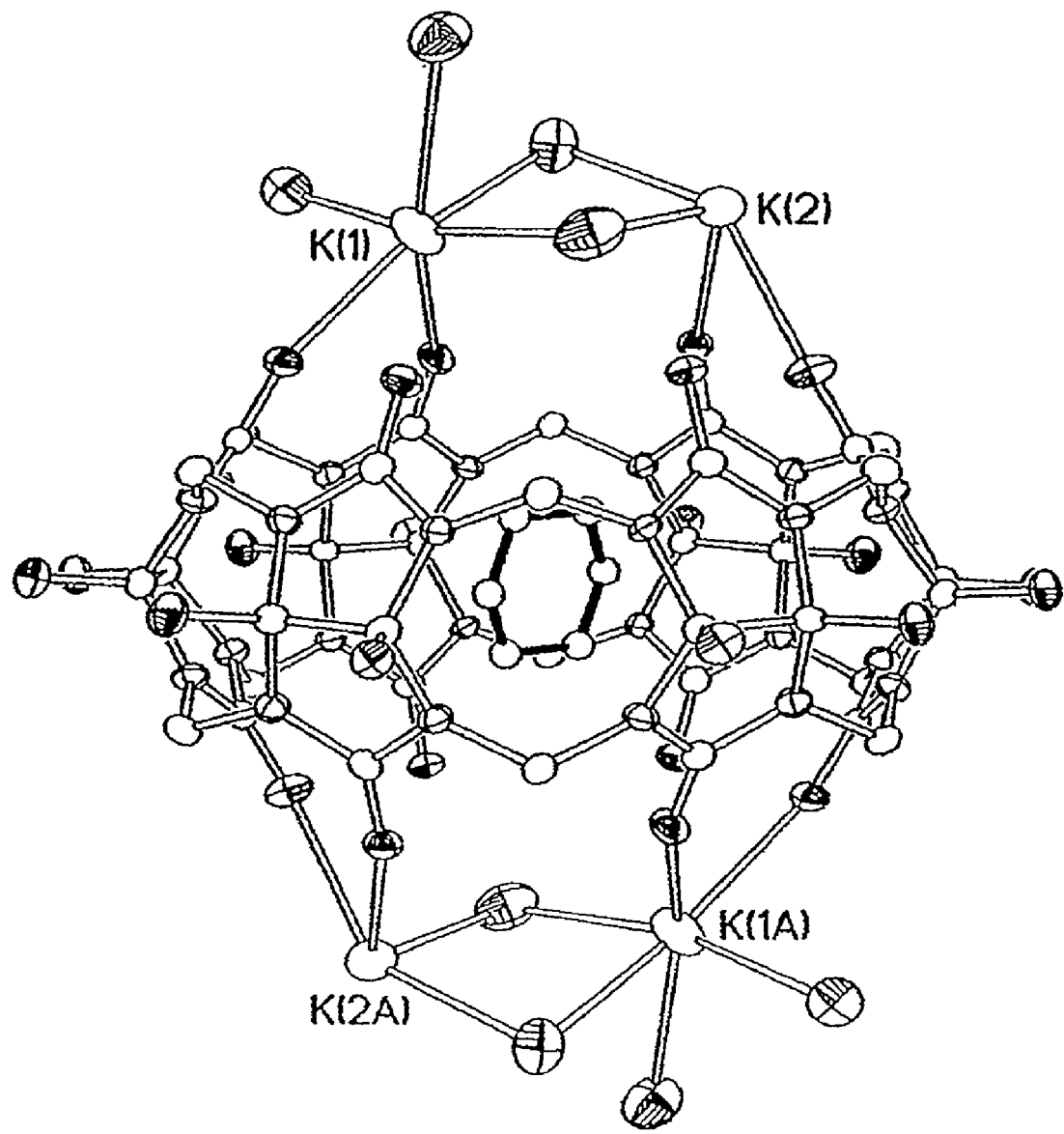
FIG. 1 is a diagram of the X-ray crystal structure of hydroxycucurbit[6]uril ($CB[6]^{OH}$) prepared in Synthesis Example 1 of the present invention.

The present invention provides hydroxycucurbituril derivatives represented by the formula 1:

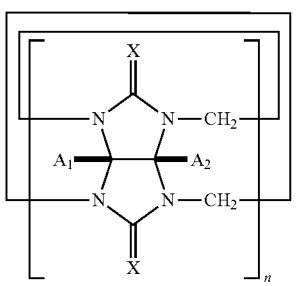
[Formula 1]

wherein n, $A_1$, $A_2$, n and X are as defined as above.

Examples of the hydroxycucurbituril derivatives represented by the formula 1 include compounds represented by formulas 2 through 4:

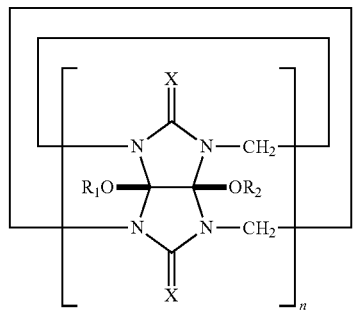
[Formula 2]

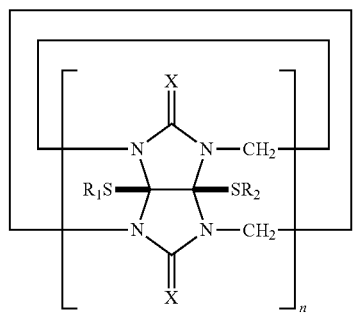
[Formula 3]

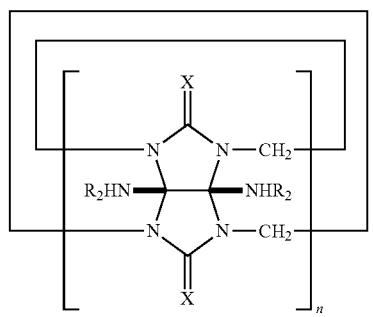
[Formula 4]

wherein $R_1$ and $R_2$ are independently selected from the group consisting of H, substituted or unsubstituted C1-C30 alkyl, substituted or unsubstituted C1-C30 alkenyl, substituted or unsubstituted C1-C30 alkynyl, substituted or unsubstituted C2-C30 carbonylalkyl, substituted or unsubstituted C1-C30 thioalkyl, substituted or unsubstituted C1-C30 alkylthiol, substituted or unsubstituted C1-C30 alkoxy, substituted or unsubstituted C1-C30 hydroxyalkyl, substituted or unsubstituted C1-C30 alkylsilyl, substituted or unsubstituted C1-C30 aminoalkyl, substituted or unsubstituted C1-C30 aminoalkylthioalkyl, substituted or unsubstituted C5-C30 cycloalkyl, substituted or unsubstituted C2-C30 heterocycloalkyl, substituted or unsubstituted C6-C30 aryl, substituted or unsubstituted C6-C20 arylalkyl, substituted or unsubstituted C4-C30 heteroaryl and substituted or unsubstituted C4-C20 heteroarylakyl, X is O, S or NH, and n is an integer between 4 and 20.

Examples of the hydroxycucurbituril derivatives represented by the formula 1 also include compounds represented by formulas 8 through 11:

[Formula 8]

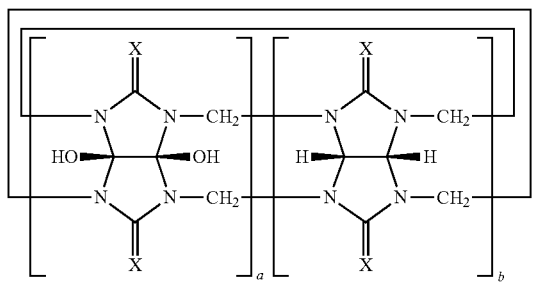

[Formula 9]

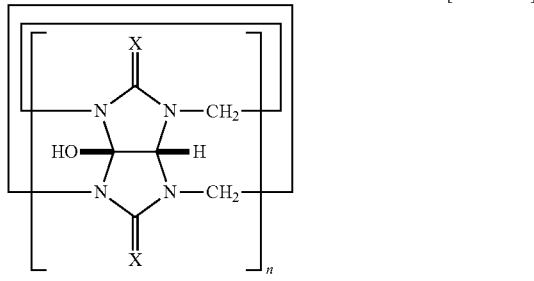

[Formula 10]

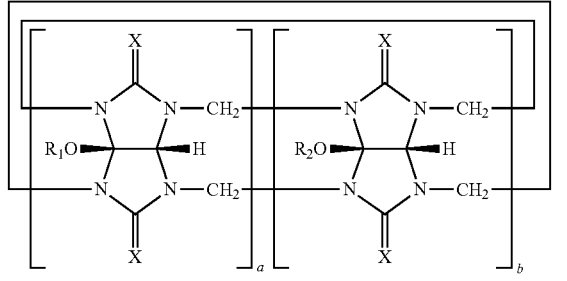

[Formula 11]

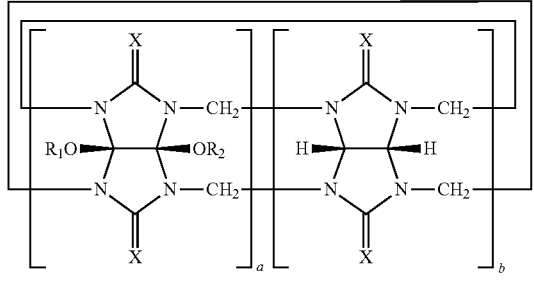

wherein X, n, $R_1$ and $R_2$ are defined as above, and a and b are integers independently in the range from 4 to 20 provided that the sum of a and b is in the range from 4 to 20.

Among the hydroxycucurbituril derivatives represented by the formula 1, more preferred examples include compounds represented in Formulas 2 through 4, wherein n is an integer between 5 and 10, and $R_1$ and $R_2$ are independently hydrogen, allyl (propylene), propynyl, C1-C30 alkyloxycarbonyl, C1-C30 alkylcarbonyl, and C1-C30 aminoalkyl.

The hydroxycucurbiturils according to the present invention represented by the Formula 5 have a hydroxy group so that various substituents can be easily introduced by alkylation and carboxylation, providing wider applications.

Examples of the compound having a substituent introduced using the hydroxycucurbituril include a compound wherein X=O, n=5~8, and $R_1$=$R_2$=butyl, a compound wherein X=O, n=5~8, and $R_1$=$R_2$=allyl, and a compound wherein X=O, n=5~8, and $R_1$=$R_2$=dodecanoyl(carbonylundecyl).

The above-mentioned compounds are highly soluble in organic solvents such as dimethylsulfoxide, chloroform, methylene chloride or methanol.

Examples of the substituents used in the present invention, i.e., unsubstituted C1-C30 alkyl, include methyl, ethyl, propyl, n-butyl, isobutyl, sec-butyl, pentyl, iso-amyl, hexyl, dodecyl and hexadecyl. One or more hydrogen atoms in the alkyl group, can be substituted by halogen atom, hydroxy, nitro, cyano, amino, amidino, hydrazine, hydrazone, carboxy or their salts; sulfonic acid or its salt; phosphoric acid or its salt; or C1-C20 alkyl, alkenyl or alkynyl, C1-C20 heteroalkyl, C6-C20 aryl, C6-C20 arylalkyl, C6-C20 heteroaryl or C6-C20 heteroarylalkyl.

The term "unsubstituted C1-C30 alkenyl or alkynyl" used as the substituent in the present invention stands for hydrocarbon groups containing at least one carbon to carbon double bond or triple bond in the middle or end portion of the chain of the alkyl as defined above. Exemplary unsubstituted such groups include ethylene, propylene, butylene, hexylene, acetylene, and the like. One or more hydrogen atoms in the alkenyl or alkynyl group can be substituted by halogen atom, hydroxy, nitro, cyano, amino, amidino, hydrazine, hydrazone, carboxy or their salts; sulfonic acid or its salt; phosphoric acid or its salt; or C1-C20 alkyl, alkenyl or alkynyl, C1-C20 heteroalkyl, C6-C20 aryl, C6-C20 arylalkyl, C6-C20 heteroaryl or C6-C20 heteroarylalkyl.

Exemplary C2-C30 carbonylalkyl groups used as the substituents in the present invention include acetyl (carbonylmethyl), butyryl (carbonylpropyl), octanoyl (carbonylheptyl), dodecanoyl (carbonylundecyl), and the like. One or more hydrogen atoms in the carbonylalkyl group can be substituted by various substituents like the hydrogen atoms in the C1-C30 alkyl group.

Exemplary C1-C30 thioalkyl groups used as the substituents in the present invention include thiobutyl, thiooctyl, thiopropyl, and the like. One or more hydrogen atoms in the C1-C30 thioalkyl group can be substituted by various substituents like the hydrogen atoms in the C1-C30 alkyl group.

Exemplary C1-C30 alkylthio groups used as the substituents in the present invention include butylthio, propylthio, octylthio, and the like. One or more hydrogen atoms in the C1-C30 alkylthio group can be substituted by various substituents like the hydrogen atoms in the C1-C30 alkyl group.

Exemplary C1-C30 hydroxyalkyl groups used as the substituents in the present invention include hydroxyethyl, hydroxybutyl, and the like. One or more hydrogen atoms in the C1-C30 alkylthio group can be substituted by various substituents like the hydrogen atoms in the C1-C30 alkyl group.

Exemplary C1-C30 alkylsilyl groups used as the substituents in the present invention include triethoxysilylpropyl, and the like. One or more hydrogen atoms in the C1-C30 alkylsilyl group can be substituted by various substituents like the hydrogen atoms in the C1-C30 alkyl group.

Exemplary C1-C30 aminoalkyl groups used as the substituents in the present invention include aminoethyl, aminobutyl, aminopropyl, and the like. One or more hydrogen atoms in the aminoalkyl group can be substituted by various substituents like the hydrogen atoms in the C1-C30 alkyl group.

The term "cycloalkyl" used as the substituent in the present invention stands for a C5-C30 monovalent monocycloalkyl group, and examples of such group include cyclohexyl, cyclopentyl, and the like. One or more hydrogen atoms in the cycloalkyl groups can be substituted by various substituents like the hydrogen atoms in the C1-C30 alkyl group.

The term "heterocycloalkyl" means a monovalent monocyclic alkyl group having 5 to 30 carbon atoms which contains 1, 2 or 3 heteroatoms selected from N, O, P and S, and the remaining ring atoms of which are carbon. Examples of such heterocycloalkyl radicals include, piperidyl, tetrahydrofuran, and the like. One or more hydrogen atoms in the heterocycloalkyl radicals can be substituted by various substituents like hydrogen atoms in the C1-C30 alkyl group.

The term "aryl" used singly or in combination as the substitutent in the present invention stands for a C6-C30 carbocycle aromatic system containing one or more rings, and such rings may be pendant from the backbone or fused together, and exemplary aryl groups include aromatic groups such as phenyl, naphthyl, tetrahydronaphthyl, indane or biphenyl, more preferably phenyl or naphthyl. The aryl group may have such substituents as hydroxy, halo, haloalkyl, nitro, cyano, alkoxy, lower alkyl amino or the like. One or more hydrogen atoms in the aryl group can be substituted by various substituents like hydrogen atoms in the C1-C30 alkyl group.

The term "heteroaryl" means an aromatic group having 6 to 30 ring atoms, which contains 1, 2 or 3 hetero atoms selected from N, O, P and S, and the remaining ring atoms of which are carbon. The term "heteroaryl" also means an aromatic group forming a quaternary salt or N-oxide which is obtained by oxidizing a heteroatom in the ring. Examples of such heteroaryl radicals include, but are not limited to, thienyl, benzothienyl, pyridinyl, pyrazinyl, pyrimidinyl, pyridazinyl, quinolinyl, quinoxalinyl, imidazolyl, furanyl, benzofuranyl, thiazolyl, isoxazolyl, benzisoxazolyl, benzimidazolyl, triazolyl, pyrazolyl, pyrrolyl, indolyl, 2-pyridonyl, 4-pyridonyl, N-alkyl-2-pyridonyl, and their equivalent N-oxides (e.g., pyridyl N-oxide or quinolinyl N-oxide), and quaternary salts thereof. One or more hydrogen atoms in the heteroaryl radicals can be substituted by various substituents like hydrogen atoms in the C1-C30 alkyls.

The term "heteroarylalkyl" means that some of hydrogen atoms in the heteroaryl group are substituted by alkyl. One or more hydrogen atoms in the heteroaryl radicals can be substituted by various substituents like hydrogen atoms in the C1-C30 alkyls.

The alkylene substituent used in the present invention are the same as alkyl substituent described above, except that it is inserted into the middle portion of a bond of the compound rather than being combined into the end portion.

Methods for preparing hydroxycucurbituril derivatives represented by the formula 1 will now be described.

Among the hydroxycucurbituril derivatives represented by the formula 1, a compound wherein $A_1$ is $OR_1$ and $A_2$ is $OR_2$, that is, a compound represented by the formula 2 can be prepared by the alkylation or carboxylation of hydroxycucurbituril represented by the formula 5:

[Formula 5]

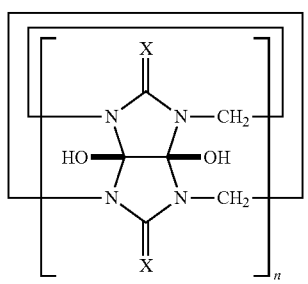

-continued

[Formula 1]

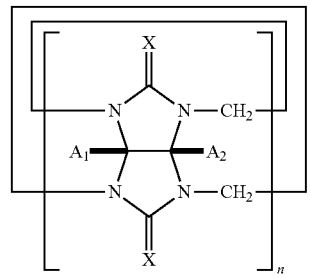

wherein X, $R_1$, $R_2$, and n are as described above.

During alkylation, usable examples include a halide selected from the group consisting of C1-C30 alkyl halide, C1-C30 alkenyl halide, C1-C30 alkynyl halide, and C1-C30 alkylcarboxylic acid anhydride. The amount of the halide is 1 to 60 moles per mole of hydroxycucurbituril represented by the formula 5.

The alkyl halide is at least one selected from the group consisting of methyl iodide, ethyl iodide, butyl bromide, and mixtures thereof. Usable examples of the alkenyl halide include allyl bromide, butenyliodide and mixtures thereof. Usable examples of the alkynyl halide include propargyl bromide, hexynyl bromide and mixtures thereof.

Examples of the alkylcarboxylic acid anhydride required for the carboxylation include acetic anhydride, butyric anhydride, dodecanoic anhydride and mixtures thereof.

During the alkylation or carboxylation, at least one base selected from the group consisting of triethylamine, potassium hydroxide, potassium carbonate and sodium hydride can be used. The amount of the base is 1 to 60 moles per mole of hydroxycucurbituril derivative represented by the formula 1.

In order to synthesize a hydroxycucurbituril derivative represented by the formula 1 wherein $R_1$ and $R_2$ are different from each other, two among alkyl halide, alkenyl halide and alkylcarboxylic acid anhydride are used together or the amounts of the halide and alkylcarboxylic acid anhydride are adjustably used.

Any solvent capable of dissolving hydroxycucurbituril can be used for the alkylation and carboxylation, and examples thereof include dimethylsulfoxide (DMSO) and dimethylformamide (DMF). The reaction temperatures of the alkylation and carboxylation can vary according to the alkyl halide used, but preferably 0 to 100° C.

A hydroxycucurbituril derivative represented by the formula 12 can be prepared by reacting hydroxycucurbituril derivative represented by formula 5 with C1-C30 alkyl halide in the presence of a base:

[Formula 12]

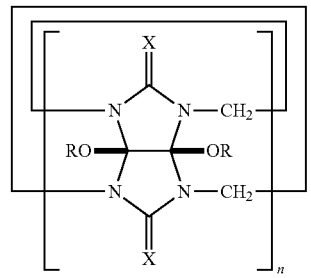

wherein R is as defined for $R_1$ above.

A hydroxycucurbituril derivative represented by the formula 13 can be prepared by reacting hydroxycucurbituril derivative represented by formula 8 with C1-C30 alkyl halide in the presence of a base:

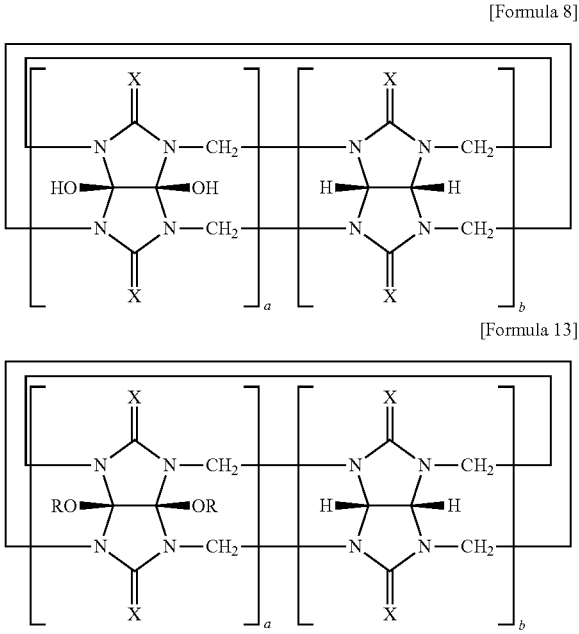

[Formula 8]

[Formula 13]

wherein R is as defined for $R_1$ above, except for the case of being hydrogen, X, a and b are as described above.

The alkyl halide is at least one selected from the group consisting of methyl iodide and butyl bromide, and potassium hydroxide, triethylamine, potassium carbonate or sodium hydride is used as the base. The amount of the halide is 1 to 60 moles and the amount of the base is 1 to 60 moles per mole of hydroxycucurbituril. DMSO or DMF is used as the solvent. The reaction temperature of the alkylation varies according to the kind of reactant used, but preferably 0 to 100° C.

If $R_1$ and $R_2$ in the formula 2 are both allyl group, a reaction with a compound represented by the formula 6 is further performed to give a compound represented by the formula 2 (where $R_1$ and $R_2$ are both —$CH_2CH_2CH_2SR'Y$).

HS—R'—Y      [Formula 6]

wherein R' is C2-C10 alkylene, and Y is —COOH, —$NH_2$, OH or SH.

The reaction conditions are not specifically limited, but photo irradiation using UV is preferred.

Examples of the compound represented by the formula 6 include $HSCH_2COOH$, $HSCH_2CH_2NH_2$ and the like.

Also, the compound represented by the formula 2 (where $R_1$ and $R_2$ are both —$CH_2CH_2OH$) can be obtained from the compound of the formula 2 (where $R_1$ and $R_2$ are both allyl group) by the oxidation using ozone and reduction using $NaBH_4$.

Among the hydroxycucurbituril derivatives represented by the formula 1, a compound wherein $A_1$ is $SR_1$ and $A_2$ is $SR_2$, that is, a compound represented by the formula 3, can be prepared by reacting the hydroxycucurbituril represented by the formula 5 with thiol compound:

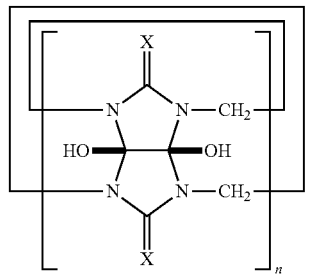

[Formula 5]

wherein X and n are as defined above.

During the reaction, an acid such as formic acid, hydrochloric acid, sulfuric acid or p-toluenesulfonic acid can be added.

Examples of the thiol compound include C1-C30 alkyl thiol, C6-C30 aryl thiol, C1-C30 hydroxyalkyl thiol or C1-C30 alkylthiol substituted with carboxylic acid, for example, benzene thiol or propylthiol. The amount of the thiol compound used is 30 to 80 moles per mole of the compound represented by the formula 5.

Among the hydroxycucurbiturils represented by the formula 1 and derivatives thereof, a compound wherein $A_1$ is $NHR_1$, and $A_2$ is $NHR_2$, that is, a compound represented by the formula 4, can be prepared by reacting the hydroxycucurbituril represented by the formula 5 with amine compound.

During the reaction, an acid such as formic acid, hydrochloric acid, sulfuric acid or p-toluenesulfonic acid can be added.

Examples of the amine compound include C1-C30 alkyl amine, C6-C30 aryl amine, C1-C30 hydroxyalkyl amine or C1-C30 alkylamine substituted with carboxylic acid, for example, propyl amine or aniline. The amount of the amine compound used is 30 to 80 moles per mole of the compound represented by the formula 1.

The hydroxycucurbituril represented by the formula 5 can be obtained by oxidizing cucurbituril represented by the formula 7:

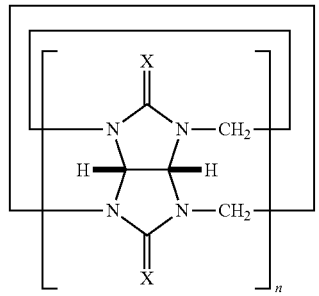

[Formula 7]

wherein X and n are as defined above.

The oxidation is performed using at least one oxidizer selected from the group consisting of $O_3$, $K_2Cr_2O_7$, $Na_2Cr_2O_7$, $KMnO_4$, $NaIO_4$, $Pb(OC(=O)CH_3)_2$, $RuO_4$, $H_2O_2$, $RuCl_3$, $CrO_3$, $(C_5H_5NH)_2Cr_2O_7(PDC)$, pyridinium-chlorochromate (PCC), $NaClO_2$, $Hg(OC(=O)CH_3)_2$, $(NH_4)_2S_2O_8$, $K_2S_2O_8$, $Na_2S_2O_8$, $NaHSO_5$, $KHSO_5$, $H_2N_2O_2$, Cytochrome P-450 enzyme, $C_6H_5IO$ and NaOCl, preferably $(NH_4)_2S_2O_8$, $K_2S_2O_8$ or $Na_2S_2O_8$. The amount of the oxidizer used is preferably 8 to 60 moles per mole of the compound represented by the formula 7.

Any solvent capable of dissolving the cucurbituril represented by the formula 7 can be used as the solvent, and examples thereof include distilled water, acidic water and so on. The amount of the solvent is 1,000 to 100,000 parts by weight based on 100 parts by weight of the cucurbituril represented by the formula 5.

In the case where $(NH_4)_2S_2O_8$, $K_2S_2O_8$ or $Na_2S_2O_8$ is used as the oxidizer, the temperature of the oxidation reaction is preferably 25 to 100° C. If the reaction temperature is higher than 100° C., a large amount of undesired byproducts is generated. If the reaction temperature is lower than 25° C., the reaction is undesirably very slow.

After the oxidation reaction, the reaction mixture is subjected to workup, thereby obtaining hydroxycucurbituril derivatives represented by the formula 5.

In the oxidation, in addition to the hydroxycucurbituril represented by the formula 5, partially oxidized hydroxycucurbituril derivatives, such as the compounds represented by the formulas 8 and 9, can be obtained by appropriately adjusting the amount of the oxidizer.

The workup for separating pure forms of the hydroxycucurbituril derivatives represented by the formulas 5, 8 and 9 from the reaction mixture is carried out as follows.

The reaction mixture containing the hydroxycucurbituril derivatives represented by the formulas 5, 8 and 9 is cooled to room temperature, and tetrahydrofuran, methanol or acetone is added thereto, followed by filtration to remove insoluble materials. Then, methanol vapor is diffused into the above filtrate, thereby to give pure crystalline materials. As described in the above, the hydroxycucurbituril is purified and isolated by the crystallization employing diffusion method.

The hydroxycucurbituril derivatives having the formula 1 according to the present invention, which can be used as a substitute for cyclodextrin, have cavities having a diameter of 4 to 15 Å, which are able to include compounds such as benzene derivatives, naphthalene derivatives, carborane derivatives, fullerene derivatives, ferrocene derivatives and adamantane derivatives in their cavities.

The hydroxycucurbiturils having the formula 1 and their derivatives can include various compounds with different sizes, and have Lewis base atoms near the cavities of the molecule, which can form complex with charged metal ions, organometallic ions or organic compounds, and thus the cucurbituril derivatives can have a wide range of applications.

The hydroxycucurbituril derivatives according to the present invention, for example, hydroxycucurbiturils having the formula 1 can be improved their solubilities in various solvents by introducing alkyloxy group instead of hydroxy group through alkylation of hydroxycucurbituril. In particular, introduction of allyl group in hydroxycucurbituril having the formula 1 can be applied to produce a polymer for chromatographic columns of gas chromatography (GC) or high performance liquid chromatography (HPLC), and as drug carriers or additives to cosmetics or food. Although cucurbituril derivatives have various advantages compared to the cyclodextrin derivatives, in practice, the cucurbituril derivatives have been used in limited applications, which is because the cucurbiturils were not able to introduce desired substituents unlike the cyclodextrin derivatives. However, the hydroxycucurbituril derivatives according to the present invention can introduce various substituents, providing wider applications than previously known cucurbituril derivatives.

In detail, the hydroxycucurbituril derivatives according to the present invention can be used to remove organic dyes from waste water, heavy metal from water, and radioactive isotopes from radioactive wastes, to capture and remove unpleasant odor, and air pollutants such as carbon monoxide, carbon dioxide, $NO_x$ and $SO_x$, and to deodorize and decolorize livestock waste water and ironwork waste water. Also, the hydroxycucurbituril derivatives having the formula 1 are applicable in manufacturing sensors for sensing ammonium ions, organic amines, amino acid derivatives, nucleic acid bases and neurotransmitters such as acetylcholine, alkali metal or alkaline earth metal ions, and ions of heavy metals such as lead or mercury. The hydroxycucurbituril derivatives having the formula 1 can also be used as additives to polymers, cosmetics, artificially scented papers or textiles, pesticides and herbicides, drugs and food, and used as drug carriers. The hydroxycucurbituril derivatives having the formula 1 can be used for extraction and purification of fullerene or caborane compounds, and used as packing materials of chromatographic columns, as additives to gas separation membranes, as catalysts for various chemical reactions.

An ion sensor using the hydroxycucurbituril represented by the formula 1 will now be described.

An ion sensor includes an ion selective membrane. The ion selective membrane is fabricated by preparing a composition for forming an ion selective membrane by dissolving an ion selective material, a polymer support and a plasticizer in a solvent, and removing the solvent from the resultant material. An ion selective electrode is fabricated using the ion selective membrane. The ion sensor can be manufactured using the ion selective electrode by common techniques.

In the composition for forming an ion selective membrane, the hydroxycucurbituril derivative represented by the formula 1 is used as the ion selective material, in an amount of 0.5 to 10 parts by weight based on the total amount of the composition. In this range, the efficiency of the manufactured ion sensor is high. The polymer support serves to support the ion selective membrane, and usable examples thereof include polyvinylchloride, polyurethane and silicon rubber. The amount of the polymer support used is preferably 10 to 90 parts by weight based on the total amount of the composition.

The plasticizer serves to make easily membrane formulation, and usable examples thereof include 2-nitrophenyloctylether, dioctyl adiphate and dioctylsebacate. The amount of the plasticizer used is preferably 10 to 70 parts by weight based on the total amount of the composition.

In some cases, the composition for forming an ion selective membrane may further include additives for improvement of sensitivity performance, and examples thereof include potassium tetrakis(4-chlorophenyl)borate, sodium tetrakis[3,5-bis(1,1,1,3,3,3-hexafluoro-2-methoxy-2-propyl)-phenyl]borate, and potassium tetrakis[3,5-bis(trifluoromethyl)-phenyl]borate.

The thus-obtained ion sensor is used to detect heavy metals such as lead, mercury, alkali earth metal or alkali metal or organic materials such as organic amines, amino acids or nucleic base.

The present invention is illustrated in more detail by the following examples and not intended to limit the scope of the invention.

EXAMPLES

Synthesis Example 1

Preparation of Hydroxycucurbit[6]uril Having the Formula 2 (X=O, n=6, $R_1$=$R_2$=H)

1.0 g of cucurbituril represented by the formula 7 (X=O, n=6, $R_1$=$R_2$=H) and 3.8 g of $K_2S_2O_8$ were added to 100 mL of distilled water and the resultant mixture was stirred at 85° C. for 12 hours.

Then, the reaction mixture was cooled to room temperature and filtered to remove insoluble materials, and tetrahydrofuran was added thereto in a mixture ratio of the filtrate to tetrahydrofuran being 1:1 by volume.

The resultant mixture was filtered to remove insoluble solid. Then methanol vapor was slowly diffused into the filtrate to give a colorless crystalline hydroxycucurtbit[6]uril in a yield of 55%.

The hydroxycucurtbit[6]uril was analyzed by X-ray structure determination, and the result thereof is shown in FIG. 1.

Referring to FIG. 1, it was confirmed that the hydroxycucurtbit[6]uril has cavity inside, and can effectively produce inclusion complexes with organic compounds:

$^1$H NMR (500 MHz, DMSO) δ: 7.86 (s, 12H), 5.34 (d, J=14.9 Hz, 12H), 4.43 (d, J=14.9 Hz, 12H);
$^{13}$C NMR (125 MHz, DMSO) δ: 152.7, 93.8, 40.2.

Synthesis Example 2

Preparation of Hydroxycucurbit[5]uril Having the Formula 2 (X=O, n=5, $R_1$=$R_2$=H)

The same procedure as in Synthesis Example 1 was carried out using cucurbituril having the formula 7 (X=O, n=5, $R_1$=$R_2$=H) instead of cucurbituril having the formula 7 (X=O, n=6, $R_1$=$R_2$=H) to give hydroxycucurbit[5]uril having the formula 2 (X=O, n=5, $R_1$=$R_2$=OH) in a yield of 45%:

$^1$H NMR (500 MHz, DMSO) δ: 8.23 (s, 10H), 5.30 (d, J=15.1 Hz, 10H), 4.47 (d, J=15.1 Hz, 10H);
$^{13}$C NMR (125 MHz, DMSO) δ: 152.9, 93.6, 40.4.

Synthesis Example 3

Preparation of Hydroxycucurbit[7]uril Having the Formula 2 (X=O, n=7, $R_1$=$R_2$=H)

The same procedure as in Synthesis Example 1 was carried out using cucurbituril having the formula 7 (X=O, n=7, $R_1$=$R_2$=H) instead of cucurbituril having the formula 7 (X=O, n=6, $R_1$=$R_2$=H) to give hydroxycucurbit[7]uril (X=O, n=7, $R_1$=$R_2$=OH) in a yield of 40%:

$^1$H NMR (500 MHz, DMSO) δ: 7.42 (s, 14H), 5.25 (d, J=15.2 Hz, 14H), 4.29 (d, J=15.2 Hz, 14H);
$^{13}$C NMR (125 MHz, DMSO) δ: 153.3, 93.5, 40.0.

Synthesis Example 4

Preparation of Hydroxycucurbit[8]uril Having the Formula 2 (X=O, n=8, $R_1$=$R_2$=H)

The same procedure as in Synthesis Example 1 was carried out using cucurbituril having the formula 7 (X=O, n=8, $R_1$=$R_2$=H) instead of cucurbituril having the formula 7 (X=O, n=6, $R_1$=$R_2$=H) to give hydroxycucurbit[8]uril (X=O, n=8, $R_1$=$R_2$=H) in a yield of 45%:

$^1$H NMR (500 MHz, DMSO) δ: 8.05 (br, 16H), 5.42 (d, J=14.9 Hz, 16H), 4.52 (d, J=14.9 Hz, 16H);
$^{13}$C NMR (125 MHz, DMSO) δ: 152.7, 93.8, 40.0.

Synthesis Example 5

Preparation of Methyloxycarbonylcucurbit[6]uril Having the Formula 2 (X=O, n=6, $R_1$=$R_2$= (C=O)CH$_3$)

1.0 g of hydroxycucurbituril (X=O, n=6, $R_1$=$R_2$=OH) prepared in Synthesis Example 1 was dissolved in 2 mL of DMSO and then 0.2 mL of acetic anhydride was added thereto. To the reaction mixture was added 0.4 mL of triethylamine, and then stirred for 4 hours at room temperature.

Then, 8 mL of ethylether was added to the reaction mixture to generate the precipitate which was filtered to give 0.14 g of a white methyloxycarbonylcucurtbit[6]uril represented by the following structural formula in a yield of 98%:

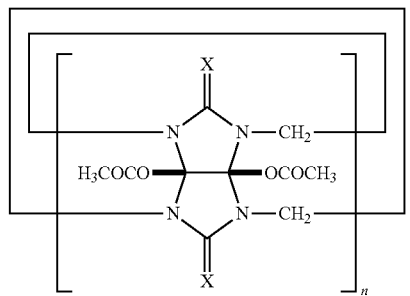

wherein n is 6:
$^1$H NMR (500 MHz, DMSO) δ: 5.57 (d, J=15.9 Hz, 12H), 4.25 (d, J=15.9 Hz, 12H), 2.19 (s, 36H).

Synthesis Example 6

Preparation of Methyloxycucurbit[6]uril Having the Formula 2 (X=O, n=6, $R_1$=$R_2$=CH$_3$)

0.1 g of hydroxycucurbituril (X=O, n=6, $R_1$=$R_2$=OH) prepared in Synthesis Example 1 was dissolved in DMSO and then 50 mg of sodium hydride and 0.1 mL of methyl iodide were added thereto, followed by stirring at room temperature for 3 hours. Then, 8 mL of ethylether was added to the reaction mixture to generate the precipitate which was filtered to give methyloxycarbonylcucurtbit[6]uril in a yield of 85%:

$^1$H NMR (500 MHz, DMSO) δ: 5.51 (d, J=15.2 Hz, 12H), 4.29 (d, J=15.2 Hz, 12H), 3.43 (s, 36H).

Synthesis Example 7

Preparation of Allyloxycucurbit[5]uril Having the Formula 2 (X=O, n=5, $R_1$=$R_2$=Allyl)

0.1 g of hydroxycucurbit[5]uril prepared in Synthesis Example 1 was dissolved in 0.1 g of DMSO and mixed with 60 mg of sodium hydride at 0° C., followed by adding 100 μL of allylbromide after 1 hour and stirring at room temperature for 10 hours. To the reaction mixture was added water to generate the precipitate which was filtered to give 0.12 g of allyloxycucurtbit[5]uril in a yield of 75%:

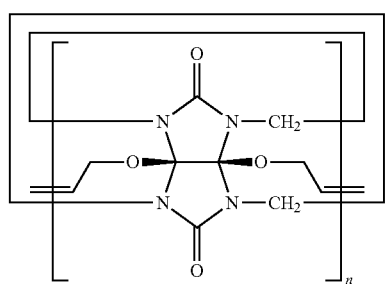

$^1$H NMR (500 MHz, DMSO) δ: 5.68-5.57 (m, 20H), 5.51-5.44 (m, 20H), 4.29 (d, J=15.2 Hz, 10H), 4.22-4.16 (m, 20H).

Synthesis Example 8

Preparation of Allyloxycucurbit[6]uril Having the Formula 2 (X=O, n=6, $R_1$=$R_2$=Allyl)

The same procedure as in Synthesis Example 7 was carried out using cucurbit[6]uril instead of cucurbit[5]uril to give the desired product:
$^1$H NMR (500 MHz, DMSO): δ: 5.72-5.67 (m, 24H), 5.56-5.50 (m, 24H), 4.29 (d, J=15.2 Hz, 12H), 4.28-4.26 (m, 24H).

Synthesis Example 9

Preparation of Allyloxycucurbit[7]uril Having the Formula 2 (X=O, n=7, $R_1$=$R_2$=Allyl)

The same procedure as in Synthesis Example 7 was carried out using cucurbit[7]uril instead of cucurbit[5]uril to give the desired product:
$^1$H NMR (500 MHz, DMSO) δ: 5.77-5.67 (m, 28H), 5.59-5.49 (m, 28H), 4.25 (d, J=15.0 Hz, 14H), 4.28-4.26 (m, 28H).

Synthesis Example 10

Preparation of Allyloxycucurbit[8]uril Having the Formula 2 (X=O, n=8, $R_1$=$R_2$=Allyl)

The same procedure as in Synthesis Example 7 was carried out using cucurbit[8]uril instead of cucurbit[5]uril to give the desired product.
$^1$H NMR (500 MHz, DMSO): δ: 5.82-5.67 (m, 32H), 5.51-5.45 (m, 32H), 4.19 (d, J=15.4 Hz, 16H), 4.26-4.24 (m, 32H).

Synthesis Example 11

Preparation of Hexa-Butyloxycucurbit[6]uril Having the Formula 2 (X=O, n=6, $R_1$=butyl, $R_2$=H)

0.1 g of hydroxycucurbit[6]uril prepared in Synthesis Example 1 was dissolved in 1 mL of dimethylformamide and 70 mg of sodium hydride added to the above solution at 0° C., followed by adding 100 μL of butylbromide after 1 hour. The resulting solution was stirred for 8 hours at 80° C. To the reaction mixture was added water to generate the precipitate which was purified using column chromatography to give 0.09 g of hexa-butyloxycucurtbit[6]uril, in a yield of 77%:
$^1$H NMR (300 MHz, DMSO) δ: 8.05 (m, 6H), 5.43 (d, J=15.0 Hz, 12H), 4.24 (d, J=15.0 Hz, 12H), 3.44 (s, 12H), 1.53 (s, 12H), 1.37 (s, 12H), 0.86 (s, 18H).

Synthesis Example 12

Preparation of Butyloxycucurbit[6]uril Having the Formula 2 (X=O, n=6, $R_1$=$R_2$=Butyl)

Stirring was performed at 80° C. for 15 hours instead of 8 hours in Synthesis Example 11 to give butyloxycucurbit[6]uril:

$^1$H NMR (300 MHz, DMSO) δ: 5.55 (d, J=15.0 Hz, 12H), 4.04 (d, J=15.0 Hz, 12H), 3.44 (s, 24H), 1.53 (s, 24H), 1.37 (s, 24H), 0.86 (s, 36H).

Synthesis Example 13

Preparation of Dihydroxycucurbit[6]uril Having the Formula 8 (X=O, a=1, b=5)

0.1 g of cucurbit[6]uril represented by the formula 7 was added to distilled water and 0.08 g of $K_2S_2O_8$ were added thereto, followed by stirring at 85° C. for 8 hours. The same workup procedure as in Synthesis Example 1 was carried out to give dihydroxycucurtbit[6]uril:
$^1$H NMR (300 MHz, DMSO) δ: 8.05 (m, 2H), 5.53-5.35 (m, 12H), 5.35-5.23 (m, 10H), 4.33-4.24 (m, 12H).

Synthesis Example 14

Preparation of Hydroxyethyloxycucurbit[6]uril Having the Formula 2 (X=O, n=6, a $R_1$=$R_2$=Hydroxyethyl)

0.1 g of allyoxycucurbit[6]uril having the formula 2 ($R_1$=$R_2$=allyl) was dissolved in 1 mL of methanol and then ozone was flowed at −78° C. The flow of ozone was stopped at the moment where the solution turned blue, and the resultant solution was subjected to oxygen stream for 10 minutes. To the resultant was added 0.2 g of $NaBH_4$ and the reaction temperature was raised to room temperature. After stirring for 10 hours, the solvent was evaporated, 1 mL of distilled water was added thereto, and 300 mg of ion exchange resin, 200 mg of cellite and 100 mg of silica gel were further added thereto, followed by stirring for 30 minutes and removing the insoluble solid. The aqueous solution was concentrated and dried to give 0.11 g of hydroxyethyloxycucurbit[6]uril represented by the following formula in a yield of 80%:

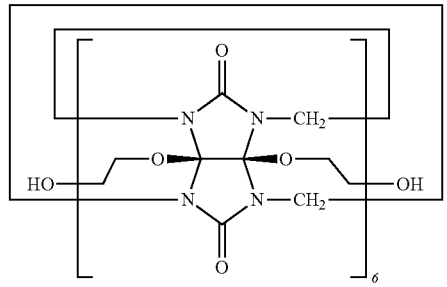

$^1$H NMR (500 MHz, $D_2O$) δ: 5.55 (d, J=15.9 Hz, 12H), 4.48 (d, J=15.9 Hz, 12H), 3.78-3.66 (m, 48H).

Synthesis Example 15

Preparation of Carboxylic Acid Substituted-Cucurbit[6]uril Having the Formula 2 (X=O, n=6, $R_1$=$R_2$=—$CH_2CH_2CH_2SCH_2COOH$)

0.1 g of allyoxycucurbit[6]uril having the formula 2 ($R_1$=$R_2$=allyl) and 250 μL of $HSCH_2COOH$ were dissolved in 1 mL of methanol, and then nitrogen was flowed to remove residual oxygen. Then, the resultant mixture was irradiated with a 300 nm UV light for 15 hours. The solvent of the reactant was evaporated to provide solid material, which was triturated with diethylether, filtered and washed with diethylether to give 0.12 g of carboxylic acid substituted-cucurbit[6]uril having the following formula (Q=—CH$_2$SCH$_2$COOH) in a yield of 82%:

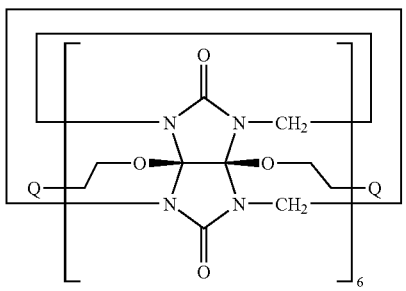

$^1$H NMR (500 MHz, DMSO) δ: 12.55 (s, 12H), 5.57 (d, J=15.0 Hz, 12H), 4.08 (d, J=15.0 Hz, 12H), 3.55 (s, 24H), 2.80 (t, J=8 Hz, 24H), 1.91 (m, 24H).

Synthesis Example 16

Preparation of Amine Substituted-Cucurbit[6]uril Having the Formula 2 (X=O, n=6, R$_1$=R$_2$= —CH$_2$CH$_2$CH$_2$SCH$_2$CH$_2$NH$_2$)

The same procedure as in Synthesis Example 15 was carried out using 200 μL of HSCH$_2$CH$_2$NH$_2$ instead of HSCH$_2$COOH to give 0.13 g of amine substituted-cucurbit [6]uril having the following formula shown in Synthesis Example 15 (Q=—CH$_2$SCH$_2$CH$_2$NH$_2$) in a yield of 80%:

$^1$H NMR (500 MHz, D$_2$O) δ: 5.68 (d, J=15.0 Hz, 12H), 3.99 (d, J=15.0 Hz, 12H), 3.54 (t, J=7 Hz, 24H), 2.86-2.84 (m, 24H), 2.51-2.42 (m, 48H), 1.89-1.85 (m, 24H).

Synthesis Example 17

The same procedure as in Synthesis Example 1 was carried out using cucurbit[6]uril having the formula 7 (X=S, n=6, R$_1$=R$_2$=H) instead of cucurbit[6]uril having the formula 7 (X=O, n=6, R$_1$=R$_2$=H) to give the desired product.

Synthesis Example 18

The same procedure as in Synthesis Example 1 was carried out using cucurbit[6]uril having the formula 7 (X=NH, n=6, R$_1$=R$_2$=H) instead of cucurbit[6]uril having the formula 7 (X=O, n=6, R$_1$=R$_2$=H) to give the desired product.

Practically, the same methods as in Synthesis Examples 17 and 18 were applied to obtain a cucurbituril compound having the formula 2 (n=5, X=S, R$_1$, R$_2$=H), a cucurbituril compound having the formula 2 (n=7, X=S, R$_1$, R$_2$=H), a cucurbituril compound having the formula 2 (n=8, X=S, R$_1$, R$_2$=H), a cucurbituril compound having the formula 2 (n=5, X=NH, R$_1$, R$_2$=H), a cucurbituril compound having the formula 2 (n=7, X=NH, R$_1$, R$_2$=H) and a cucurbituril compound having the formula 2 (n=8, X=NH, R$_1$, R$_2$=H) to use the corresponding starting materials, respectively.

Synthesis Example 19

0.1 g of hydroxycucurbit[6]uril having the formula 2 (X=O, n=6, R$_1$=R$_2$=H) prepared in Synthesis Example 1 and 0.4 mL of dodecanoic anhydride were dissolved in 2 mL of dimethylsulfoxide (DMSO). Then, 0.4 mL of triethylamine was added to the mixture and stirred for 3 days at 85° C. Thereafter, water was added to the reaction mixture to precipitate, which was filtered, washed with water and recrystallized from chloroform and hexane to give 0.14 g of white undecyloxycarbonylcucurbit[6]uril represented by the following structure (R=carbonylundecyl) in a yield of 86%:

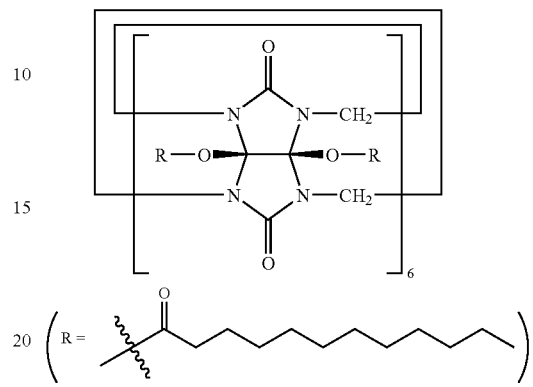

$^1$NMR (300 MHz, (DMSO+CDCl$_3$ 1:1) δ: 5.53 (d, J=12.2 Hz, 12H), 4.19 (d, J=12.6 Hz, 12H), 2.48 (m, 24H), 1.35 (m, 24H), 1.17 (m, 192H), 0.76 (t, 36H).

Synthesis Example 20

Preparation of Phenylthio-Cucurbit[6]uril Having the Formula 3 (X=O, n=6, R$_1$=R$_2$=Phenyl)

0.1 g of hydroxycucurbit[6]uril having the formula 2 (X=O, n=6, R$_1$=R$_2$=H) prepared in Synthesis Example 1 was dissolved in a mixed solvent of 0.5 mL of formic acid and 1 mL of water, and then 100 μL of benzenethiol was slowly added thereto at 0° C., followed by slowly raising the reaction temperature to room temperature and stirring for 5 hours. Then, the solvent was evaporated to give the solid material, which was filtered and washed with water several times. The recrystallization was carried out to give 0.12 g of white phenylthio-cucurbit[6]uril having the formula 3 (X=O, n=6, R$_1$=R$_2$=phenyl) in a yield of 88%:

$^1$H NMR (500 MHz, DMSO) δ: 7.45-7.12 (m, 60H), 5.53 (d, J=14.4 Hz, 12H), 4.2 (d, J=14.4 Hz, 12H).

Synthesis Example 21

Preparation of Propylamino-Cucurbit[6]uril Having the Formula 4 (X=O, n=6, R$_1$=R$_2$=Propyl)

The same procedure as in Synthesis Example 20 was carried out using propylamine instead of benzenethiol to give propylamino-cucurbit[6]uril having the formula 4 (X=O, n=6, R$_1$=R$_2$=propyl):

$^1$H NMR (500 MHz, DMSO) δ: 5.53 (m, 24H), 4.2 (d, J=14.4 Hz, 12H), 3.64-3.61 (m, 24H), 1.82-1.77 (m, 24H), 1.2 (t, J=8 Hz, 36H).

Example 1

6.6 mg of hydroxycucurbit[6]uril (CB[6]$^{OH}$) prepared in Synthesis Example 1 and 10 μL of tetrahydrofuran were dissolved in 0.5 mL of D$_2$O. Quantitative formation of a 1:1 host-guest complex was confirmed.

Example 2

6.6 mg of hydroxycucurbit[6]uril (CB[6]$^{OH}$) prepared in Synthesis Example 1 and 10 μL of cyclopentane were dissolved in 0.5 mL of D$_2$O. Quantitative formation of a 1:1 host-guest complex was confirmed.

Example 3

6.6 mg of hydroxycucurbit[6]uril (CB[6]$^{OH}$) prepared in Synthesis Example 1 and 1.2 mg of p-toluidine were dissolved in 0.5 mL of D$_2$O. Quantitative formation of a 1:1 host-guest complex was confirmed.

Example 4

6.6 mg of hydroxycucurbit[6]uril (CB[6]$^{OH}$) prepared in Synthesis Example 1 and 1.5 mg of p-toluidine hydrochloride were dissolved in 0.5 mL of D$_2$O. Quantitative formation of a 1:1 host-guest complex was confirmed.

Example 5

6.6 mg of hydroxycucurbit[6]uril (CB[6]$^{OH}$) prepared in Synthesis Example 1 and 1.2 mg of 1,4-phenylindiamine were dissolved in 0.5 mL of D$_2$O. Quantitative formation of a 1:1 host-guest complex was confirmed.

It was confirmed from Examples 1-5 that the hydroxycucurbituril derivatives prepared in Synthesis Example 1 could be advantageously used for extraction, separation and purification of organic materials.

Example 6 shows that the hydroxycucurbituril derivatives prepared in Synthesis Example 1 can capture gases in their cavities.

Example 6

6.6 mg of hydroxycucurbit[6]uril (CB[6]$^{OH}$) prepared in Synthesis Example 1 was dissolved in 0.5 mL of D$_2$O, and isobutene gas was injected thereto, thereby forming a 1:1 host-guest complex.

To investigate whether the hydroxycucurbituril derivatives prepared in Synthesis Example 1 can effectively transport physiologically active materials or drugs, the following example was carried out using acetylcholine chloride as a neurotransmitter.

Example 7

6.6 mg of hydroxycucurbit[6]uril (CB[6]$^{OH}$) prepared in Synthesis Example 1 and 2.0 mg of acetylcholine chloride were dissolved in 0.5 mL of D$_2$O, thereby forming a 1:1 host-guest complex.

Since the hydroxycucurbituril derivatives obtained in Synthesis Example 1 have Lewis base atoms near the cavities of the molecule, they can effectively form a complex with metal ions or positively charged organic compounds. With these features, in order to investigate whether the hydroxycucurbituril derivatives having this property can be applied in manufacturing sensors for sensing metal ions or ammonium ions, the following example was carried out.

Example 8

A 0.05 M Tris-buffered solution of pH 7.2 was prepared, and then a 5.5 mM hydroxycucurbit[5]uril (CB[5]$^{OH}$) solution prepared in Synthesis Example 2 and 110 mM of a KCl solution were prepared. Then, the binding constants of the cucurbit[5]uril derivative was measured using a microcalorimeter (VP-ITC, manufactured by MicroCal). As a result, it demonstrates that hydroxycucurbituril derivatives can be used as ion sensors because they could selectively bind with alkali metal ions, as well as with ammonium ions.

To investigate whether ammonium ions present in an organic solvent can bind with CB[5]$^{OH}$, the following example was carried out.

Example 9

5.5 mg of CB[5]$^{OH}$ prepared in Synthesis Example 2 and 6.7 mg of (NH$_4$)$^+$(BPh$_4$)$^-$ were dissolved in 0.5 mL CD$_3$CN. Then, ammonium ions in (NH$_4$)$^+$(BPh$_4$)$^-$ could bind with CB[5]$^{OH}$ in an acetonitrile solution.

The following example demonstrates the fabrication method of ion selective membrane and its selective sensitivity to harmful heavy metals such as lead ion using CB[5]$^{OH}$ prepared in Synthesis Example 2.

Example 10

A solution obtained by dissolving 1% by weight of CB[5]$^{OH}$ prepared in Synthesis Example 2 in 0.1 mL of methanol, 33% by weight of polyvinylchloride used as a polymer support, 65.6% by weight of 2-nitrophenyloctylether used as a plasticizer and 0.4 mL of tetrahydrofuran dissolved in 0.4% by weight of potassium tetrakis(4-chlorophenyl)borate, were homogenously mixed, followed by slowly removing the solvent, to form an ion selective membrane. An ion selective electrode was fabricated with this ion selective membrane. An electrode with a silver wire coated with silver chloride in a 0.05 M aqueous KCl solution was used as a reference electrode.

The reference electrode and the ion selective electrode were immersed in 250 mL of 1 mM Mg(OAc)$_2$—HCl buffered solution (pH=4), followed by continuously stirring for at least 1 hour until a membrane boundary potential was stabilized. Thereafter, potential differences were measured with adding lead ions to increase the concentration by 10 fold in the range of $10^{-6}$ M to $10^{-3}$ M using a micropipet at an interval of 100 seconds The result demonstrates that the ion selective electrode using CB[5]$^{OH}$ prepared in Synthesis Example 2 could be used in detecting harmful heavy metal ions remaining in water, e.g., lead or mercury ions.

The following example demonstrates the fabrication method of ion selective membrane and its selective sensitivity to neurotransmitters such as acetylcholine using CB[6]$^{OH}$ prepared in Synthesis Example 1.

Example 11

A solution obtained by dissolving 1% by weight of CB[6]$^{OH}$ prepared in Synthesis Example 1 in 0.1 mL of methanol, 33% by weight of polyvinylchloride used as a polymer support, 65.6% by weight of 2-nitrophenyloctylether used as a plasticizer and 0.4 mL of tetrahydrofuran dissolved in 0.4% by weight of potassium tetrakis(4-chlorophenyl)borate, were homogenously mixed, followed by removing the solvent slowly, to form an ion selective membrane. An ion selective electrode was fabricated with this ion selective membrane. An electrode with a silver wire coated with silver chloride in a 0.05 M aqueous KCl solution was used as a reference electrode.

The reference electrode and the ion selective electrode were immersed in 250 mL of 0.05 M Tris-HCl buffered solution (pH=7.2), followed by continuously stirring for at least 1 hour until a membrane boundary potential was stabilized. Thereafter, potential differences were measured with adding acetylcholine to increase the concentration by 10 fold in the range of $10^{-6}$ M to $10^{-1}$ M using a micropipet at an interval of 100 seconds. The selectivity to lead ions was measured in a concentration of 0.01 M by a fixed solution method.

The result demonstrates that the ion selective electrode using $CB[6]^{OH}$ prepared in Synthesis Example 1 could be used in clinical analysis by selective detection of a neurotransmitter in vivo, e.g., acetylcholine.

Example 12

1% by weight of allyoxycucurbit[6]uril prepared in Synthesis Example 8, 33% by weight of polyvinylchloride and 66% by weight of 2-nitrophenyloctylether were dissolved in THF to form a membrane. With this membrane, an ion selective electrode was fabricated. Then, the responses of the electrode with respect to ammonium ion, potassium ion, sodium ion, choline ion and acetylcholine ion were measured in a 0.01M Tris-buffered solution. As a result, the selectivity of choline with respect to acetylcholine was −1.84, ammonium ion −1.31, potassium ion −0.90 and sodium ion −1.16, respectively. The allyloxycurcubit[6]uril according to the present invention can be advantageously used in clinical analysis by selective detection of a neurotransmitter in vivo, e.g., acetylcholine, instead of choline which is a major obstacle in analyzing acetylcholine. The ion selective electrode using allyoxycucurbit[6]uril can be used in measuring acetylcholine in a concentration range of $2.1 \times 10^{-6}$ M.

As described above, since the hydroxycucurbituril derivatives of the present invention can easily introduce functional groups thereto, they have wide applications. Also, since the hydroxycucurbituril derivatives according to the present invention can be easily prepared, mass production thereof is possible for industrial purposes. Further, the hydroxycucurbituril derivatives of the present invention are applied to remove organic dyes from waste water, heavy metal from water and radioactive isotopes from radioactive wastes, to capture and remove unpleasant odor, and air pollutants such as carbon monoxide, carbon dioxide, nitrogen oxide and sulfur oxide, and to deodorize and decolorize livestock waste water and ironwork waste water. Also, the hydroxycucurbituril derivatives are applicable in manufacturing sensors for sensing ammonium ions, organic amines, amino acid derivatives, nucleic acids and neurotransmitters such as acetylcholine, alkali metal or alkaline earth metal ions, and ions of heavy metals such as lead or mercury. The hydroxycucurbituril derivatives can also be used as additives to polymers, cosmetics, artificially scented papers or textiles, pesticides and herbicides, and drugs, and used as drug carriers. The hydroxycucurbituril derivatives can be used for the extraction and purification of fullerene or caborane compounds, and used as packing materials of chromatographic columns, as additives to gas separation membranes, as catalysts for various chemical reactions. In particular, the hydroxycucurbituril derivatives can be advantageously used to detect physiologically active materials in vivo, e.g., acetylcholine. Also, since the solubility in organic solvents can be adjusted, the hydroxycucurbituril derivatives can be used as chemical reaction sites. Further, since an ion selective electrode can be easily prepared, an ion sensor that is directly applied for clinical analysis or detection of environmentally contaminating materials, can be fabricated with hydroxycucurbituril derivative.

What is claimed is:

1. The hydroxycucurbituril derivative represented by the formula 2

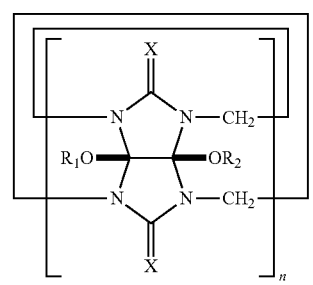

[Formula 2]

wherein $R_1$ and $R_2$ are independently H, substituted or unsubstituted C1-C30 alkyl, substituted or unsubstituted C1-C30 alkenyl, substituted or unsubstituted C2-C30 carbonylalkyl, or substituted or unsubstituted C1-C30 hydroxyalkyl X is O, and n is an integer between 4 and 20.

2. The hydroxycucurbituril derivative according to claim 1, wherein the $R_1$ and $R_2$ are independently H, methyl, allyl, propynyl, butyl, C1-C30 alkyloxycarbonyl, C1-C30 alkylcarbonyl or C1-C30 aminoalkyl.

3. The hydroxycucurbituril derivative of claim 1, wherein $R_1$ and $R_2$ are each H.

4. The hydroxycucurbituril derivative of claim 1, wherein $R_1$ and $R_2$ are each alkyl and n is 5.

5. The hydroxycucurbituril derivative according to claim 1, wherein when $R_1$ or $R_2$ is substituted C1-C30 alkyl, substituted C1-C30 alkenyl, substituted C1-C30 carbonylalkyl, or substituted C1-C30 hydroxyalkyl, one or more hydrogen atoms of the alkyl, alkenyl, cabonylalkyl, or hydroxyalkyl group are substituted by a functional group independently selected from: halogen, hydroxy, nitro, cyano, amino, amidino, hydrazine, hydrazone, carboxy or their salts; sulfonic acid or its salt;

phosphoric acid or its salt, C1-C20 alkyl, C1-C20 alkenyl, C1-C20 alkynyl, C1-C20 heteroalkyl, C6-C20 aryl, C6-C20 arylakyl, C6-C20 heteroaryl, and C6-C20 heteroarylakyl.

6. A method of preparing a hydroxycucurbituril derivative represented by the formula 2 comprising; conducting an alkylation or carboxylation reaction of hydroxycucurbituril represented by the formula 5:

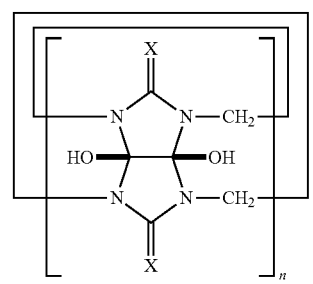

[Formula 5]

[Formula 2]

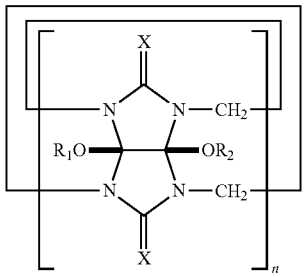

wherein $R_1$ and $R_2$ are independently H, substituted or unsubstituted C1-C30 alkyl, substituted or unsubstituted C1-C30 alkenyl, substituted or unsubstituted C2-C30 carbonylalkyl, substituted or unsubstituted C1-C30 hydroxyalkyl, X is O, and n is an integer between 4 and 20.

7. The method according to claim 6, wherein during the alkylation or carboxylation reaction, a halide selected from the group consisting of C1-C30 alkyl halide, C1-C30 alkenyl halide, C1-C30 alkynyl halide, C1-C30 alkyl carboxylic acid anhydride is used.

8. The method according to claim 6, wherein if $R_1$ and $R_2$ in the formula 2 are both allyl group, the reaction of hydroxycucurbituril derivative of the formula 2 ( n=6, $R_1$=$R_2$=allyl) with a compound represented by the formula 6 is further performed to give a compound represented by the formula 1 (where $R_1$ and $R_2$ are both —CH$_2$CH$_2$CH$_2$SR'Y)

HS—R'—Y  [Formula 6]

wherein R' is C2-C10 alkylene, and Y is —COOH, —NH$_2$, OH or SH.

9. The method according to claim 6, wherein if $R_1$ and $R_2$ in the formula 2 are both allyl group, the compound represented by the formula 2 (where $R_1$ and $R_2$ are both —CH$_2$CH$_2$OH) can be obtained by further performing oxidation and reduction of hydroxycucurbituril derivative of the formula 2 ( n=6, $R_1$=$R_2$=allyl).

10. The method according to claim 6, wherein the hydroxycucurbituril represented by the formula 5 is obtained by oxidation of cucurbituril represented by the formula 7:

[Formula 7]

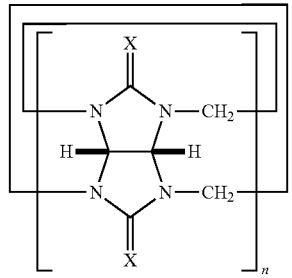

wherein X is O, S or NH and n is an integer between 4 and 20.

11. The method according to claim 10, wherein the oxidation reaction is carried out using at least one oxidizer selected from the group consisting of $O_3$, $K_2Cr_2O_7$, $Na_2Cr_2O_7$, $KMnO_4$, $NaIO_4$, $Pb(OC(=O)CH_3)_2$, $RuO_4$, $H_2O_2$, $RuCl_3$, $CrO_3$, $(C_5H_5NH)_2Cr_2O_7$(PDC), pyridiniumchlorochromate (PCC), $NaClO_2$, $Hg(OC(=O)CH_3)_2$, $(NH_4)_2S_2O_8$, $K_2S_2O_8$, $Na_2S_2O_8$, $Na_2S_2O_8$, $NaHSO_5$, $KHSO_5$, $H_2N_2O_2$, Cytochrome P-450 enzyme, $C_6H_5IO$ and NaOCl.

12. The method according to claim 10, wherein the oxidation reaction is carried out using $(NH_4)_2S_2O_8$, $K_2S_2O_8$ or $Na_2S_2O_8$, the reaction temperature is in the range of 25 to 100° C., and the amount of the oxidizer used is 8 to 60 moles per mole of the cucurbituril represented by the formula 7.

13. The method according to claim 10, wherein the hydroxycucurbituril is purified and isolated by the crystallization employing diffusion method, in which tetrahydrofuran, methanol or acetone is added to the crude hydroxycucurbituril solution and then methanol vapor is diffused into the solution after removing the insoluble materials.

* * * * *